(12) United States Patent
Maheshwari

(10) Patent No.: US 8,596,148 B2
(45) Date of Patent: Dec. 3, 2013

(54) AUTOMATED CASCADE IMPACTOR

(76) Inventor: Krishna Maheshwari, Waltham, MA (US)

( * ) Notice: Subject to any disclaimer, the term of this patent is extended or adjusted under 35 U.S.C. 154(b) by 286 days.

(21) Appl. No.: 12/929,051

(22) Filed: Dec. 27, 2010

(65) Prior Publication Data

US 2011/0088492 A1 Apr. 21, 2011

Related U.S. Application Data

(63) Continuation of application No. 12/247,546, filed on Oct. 8, 2008, now Pat. No. 7,926,367, which is a continuation of application No. PCT/US2007/008924, filed on Apr. 10, 2007.

(60) Provisional application No. 60/744,663, filed on Apr. 11, 2006.

(51) Int. Cl.
*G01N 1/22* (2006.01)

(52) U.S. Cl.
USPC ..................................... 73/863.22

(58) Field of Classification Search
USPC ........................ 73/863.22; 209/138
See application file for complete search history.

(56) References Cited

U.S. PATENT DOCUMENTS

| | | | | |
|---|---|---|---|---|
| 6,453,758 | B1 | 9/2002 | Marple et al. | 73/863.22 |
| 6,723,568 | B1 | 4/2004 | Liu et al. | 436/174 |
| 7,669,488 | B2 | 3/2010 | Bridge et al. | 73/863.22 |
| 2005/0266415 | A1 | 12/2005 | Ryan | 435/6.19 |
| 2012/0247233 | A1* | 10/2012 | Maheshwari et al. | 73/863.22 |

FOREIGN PATENT DOCUMENTS

EP 1471344 10/2004

\* cited by examiner

*Primary Examiner* — Peter Macchiarolo
*Assistant Examiner* — Tamiko Bellamy
(74) *Attorney, Agent, or Firm* — Law Offices of Steven W. Weinrieb

(57) ABSTRACT

An automated cascade impactor comprises an extension mechanism operable to couple to a plurality of impactor stages. The extension mechanism is operable to compress and separate impactor stages of the plurality of impactor stages via automation. The system provides a plurality of isolation stages operable to be automatically inserted between respective impactor stages when the impactor stages are separated by the extension mechanism. The system provides the plurality of isolation stages to be automatically compressed between impactor stages to isolate each impactor stage from at least one adjacent impactor stage. The plurality of isolation stages is operable to be automatically uncompressed and removed from between the impactor stages. The isolation stages allow automated extraction of particulate matter, cleaning and drying of interior surfaces of each impactor stage.

21 Claims, 13 Drawing Sheets

```
200 — AUTOMATICALLY COMPRESS TOGETHER
       A PLURALITY OF IMPACTOR STAGES
              ↓
201 — RECEIVE PARTICULATE MATTER DISPENSED
       INTO THE PLURALITY OF IMPACTOR STAGES
       WHILE THEY ARE COMPRESSED
              ↓
202 — AUTOMATICALLY SEPARATE
       THE IMPACTOR STAGES
              ↓
203 — AUTOMATICALLY INSERT A
       PLURALITY OF ISOLATION STAGES
       BETWEEN IMPACTOR STAGES
              ↓
204 — AUTOMATICALLY COMPRESS THE IMPACTOR
       STAGES AND INSERTED ISOLATION STAGES
       TO ISOLATE EACH IMPACTOR STAGE FROM
       AT LEAST ONE ADJACENT IMPACTOR STAGE
              ↓
205 — SUPPLY AND EXTRACT A FLUID COLLECTION AGENT,
       VIA EACH ISOLATION STAGE, TO THE INTERNAL
       VOLUME OF A RESPECTIVE IMPACTOR STAGE TO
       ENABLE SUSPENSION AND EXTRACTION, WITHIN THE
       FLUID COLLECTION AGENT, OF THE PARTICULATE
       MATTER DISPOSED ON INTERNAL SURFACES OF
       THAT ISOLATED IMPACTOR STAGE
              ↓
206 — SUPPLY AND EXTRACT A FLUID CLEANING AGENT, VIA
       EACH ISOLATION STAGE, TO THE INTERNAL VOLUME
       OF A RESPECTIVE IMPACTOR STAGE TO ENABLE
       CLEANING OF THAT ISOLATED IMPACTOR STAGE
              ↓
207 — SUPPLY A FLUID DRYING AGENT TO THE INTERNAL
       VOLUME OF A RESPECTIVE ISOLATED IMPACTOR
       STAGE TO ENABLE DRYING OF INTERNAL
       SURFACES OF THAT ISOLATED IMPACTOR STAGE
              ↓
208 — UNCOMPRESS AND SEPARATE ISOLATION
       STAGES AND IMPACTOR STAGES,
       REMOVING ISOLATION STAGES FROM
       BETWEEN IMPACTOR STAGES
```

REPEAT FOR NEW DOSE SAMPLE

FIG. 7

AUTOMATED CASCADE IMPACTOR

CROSS REFERENCE TO RELATED APPLICATIONS

This Patent Application is a continuation of U.S. application Ser. No. 12/247,546, which was filed on Oct. 8, 2008, which is also a continuation of PCT/US2007/08924 filed on Apr. 10, 2007 which claims priority to Provisional Application 60/744,663 filed on Apr. 11, 2006, entitled, "AUTOMATED CASCADE IMPACTOR", the contents and teachings of which are hereby incorporated by reference in their entirety.

FIELD OF INVENTION

Embodiments disclosed herein relate to the field of measurement of particle sizes in fluids. Example embodiments include devices and methods for measurement of particle sizes in an air sample, wherever the sample is derived. More specifically embodiments disclosed herein are related to measurement of particle sizes from dose samples of inhalation devices.

BACKGROUND OF THE INVENTION

A conventional Cascade Impactor is a device used to determine the aerodynamic particle size distribution and mass concentration levels of solid particulates and liquid aerosols, from aerosolized dry powder and aerosolized liquid drug samples injected into the Cascade Impactor. Cascade Impactors are also used by the environment control and monitoring industry to determine particulate distributions from air samples. A variety of cascade impactors are commercially available. One reason for using Cascade Impactors in a testing environment is that air flowing inside the Cascade Impactors simulates air flowing into a human lung.

When delivering drugs through the respiratory tract to the lungs, whether in the form of micro ionized powders, or in the form of micron sized droplets of aerosolized mist from a solution, it is important to know the particle size distribution of the drug. Only drug particles of sizes generally less then 5 microns in diameter can penetrate deep into the lungs, and into the bronchi. Bigger particle sizes get ingested, and excreted out of the human body. The deep lung provides an enormous amount of surface area for the active drug substance to get absorbed in the blood steam, and thus permits the efficacious use of lower doses of drugs to get the same or better physiological response than drug delivery through the oral drug delivery route. Measurement of particle size distribution from injection of the drug into the Cascade Impactors is called a Dose Determination. The Dose Determination data from the Cascade Impactors is an integral part of a submission to the FDA as part of the NDA. Thousands of Dose Determinations need to be done, in order to meet the FDA's submission criteria for a new inhalation drug. Following the drug approval, thousands of Cascade Impactors tests are still needed to be performed over the lifetime of the inhalation drug, as an on-going quality control measure to continually prove to the FDA that the performance of the inhalation drug continues to meet the approval criteria of the drug.

Thus, in order to judge how efficacious the inhalation drug is when using inhalation devices, it becomes vitally important to generate the particle size distribution of doses of drugs delivered, and to fine tune the formulation of the inhalation drug.

Of the variety of Cascade Impactors commercially available, the conventional Andersen Cascade Impactor is the most popular. However, obtaining a Dose Determination from the Andersen Cascade Impactor it is very labor intensive, and therefore, an expensive process. Each Dose Determination from a contract lab can cost upwards of $1000. Typical throughput from each analyst operating an impactor to obtain a dose determination is two Dose Determinations per day. In addition, there are many parts that need to be carefully disassembled, and washed during use of a conventional cascade impactor to obtain a Dose Determination. Samples must be manually and very carefully collected from some of the impactor parts, and those parts must then be manually assembled again in preparation of the next Dose Determination. Therefore, manually determining a Dose Determination from the Andersen Cascade Impactor is very error prone and time consuming.

Conventional Andersen Cascade Impactors on the market today are fabricated using either Aluminum or Stainless Steel. A conventional Andersen Cascade Impactor is made up of a variable number of classification or impactor stages consisting of a series of jets and Impaction Plates. The number of Impactor Stages and Impaction Plates used to make up a column of the Andersen Cascade Impactor are variable, and depend on the drug and the particle size ranges that are to be measured. The Impaction Stages are stacked on top of each other, with succeeding Impaction Stages having smaller orifice diameters. Below each Impactor Stage is an Impaction Plate. During operation, as the drug suspended in an aerosol stream is delivered into the throat of the impactor and into the set of impaction stages, at each Impaction Stage, the aerosol stream passes through the jets or orifices and impacts upon the Impaction Plate.

Each Impactor Stage contains a multitude of orifices of the same diameter for that stage. Particles in the aerosol stream with significant inertia will settle upon the Impaction Plate for a given stage, while smaller particles pass as aerosols on to the next jet Impactor Stage. By designing consecutive Impactor Stages with higher aerosol jet velocities, smaller diameter particles are collected at each subsequent Impactor Stage (e.g. upon the impactor plate for that stage) giving the cascade affect of separation. The bottommost or lowest Impactor Stage contains a filter, to collect any drug that has not been collected on the Impaction Plates or the Impactor Stages. Typically the filter utilized is made of fiber media, or a very fine stainless steel mesh.

Sandwiched between succeeding stages is an O-Ring, so that all of the airflow is through the Impactor Stages, and none of the airflow leaks out of a seal formed between each impactor stage. Preventing airflow from leaking out of the Impactor is very important for obtaining reproducible experimental results. The Impactor Stages in a conventional impactor are tightly held by spring-loaded clamps, spaced 120 degrees apart around the circumference of the impactor, to ensure uniform closing pressure, and thus keeping the Impactor Stages tightly sealed. At the top of the stage assembly is a Pre-Separator Stage that simulates the back of the throat. The Pre-Separator Stage is where the bulk of the larger particle sizes are collected. Above the Pre-Separator is a Glass-Entry Throat. The inhaler is fitted into the Glass Entry Throat using an adapter.

The particle size range collected at each of the Impactor Stages depends on the jet orifice velocity of the specific Impactor Stage, the distance between the orifices and the collection surface, and the collection characteristics of the preceding Impactor Stage.

The combination of a constant flow rate, and successively smaller diameter orifices increase the velocity of sample air as it cascades through the Andersen Cascade Impactor, resulting in the impaction of progressively smaller particles in the succeeding Impactor Stages.

To operate the conventional Andersen Cascade Impactor, vacuum is applied to the bottommost Impactor Stage containing the filter, and a constant airflow is established through the Andersen Cascade Impactor. The inhaler is attached to the Glass Entry Throat on top of the Pre-Separator, and the drug is "inhaled" by the Impactor by dispensing one dose of the drug within the aerosol stream emitted from the inhaler into the throat of the impactor via the mouthpiece adapter. As the drug particles of differing particle size within the aerosol stream pass through the impactor, the particles get deposited onto different Impaction Plates, with the bigger particles on the top and smaller particles on the bottom Impaction Plates. After dispensing a single dose of the drug into the impactor, the Impaction Plates and the Impactor Stages are then manually disassembled by hand and each one of them carefully washed with solvent. Samples are collected in duplicate from each collection plate surface in the Andersen Cascade Impactor, and an analyst in the testing lab manually applies an HPLC technique to determine the drug content or collection amount of the surface for a given stage. The inhaler is weighed before and after drug injection into the Automated Andersen Cascade Impactor. Assuming mass balance, the particle size is deduced from the layer it was collected and the particle size distribution for the dose is drawn up.

Particle sizes less then 3-5 microns are the particles that travel deep into the lungs, permitting ready absorption of the drug into the blood, and thus are most efficacious. For this reason the US FDA and other regulatory agencies throughout the world require extensive particle size distribution data from the drug companies. At about two Dose Determinations per day using a conventional cascade impactor that operates by performing the test manually, it can take years to generate the data and get regulatory approval from the FDA.

SUMMARY OF THE INVENTION

Conventional technologies for obtaining particle size distribution data using conventional cascade impactors suffer from a variety of deficiencies. In particular, obtaining particle size distribution using conventional impactors provides very low throughput since conventional impactors rely on completely manual setup, operation, testing and dose determination. Additionally, the manual process is very prone to a great degree of operator induced variability in the data produced. Each operator (e.g. lab technician or analyst) washes the many components of the Andersen Cascade Impactor a little differently, thus causing inconsistency in the amount of drug collected from each stage and each Impaction plate. This inconsistent human washing of the plurality of impactor surfaces further affects the recovery of a drug from the same apparatus for subsequent Dose Determinations. This operator induced variability precipitates the need for additional Dose Determinations that cause delay in submission of data by the drug companies to the FDA, and thus also delay the approval of drugs by the FDA. Delays due to operator induced variability, and low throughput due to manual operations of the ACI can cause the loss of hundreds of millions of dollars in lost revenue.

Embodiments disclosed herein significantly overcome such deficiencies and provide an Automated Cascade Impactor that allows multiple Dose Determinations per day, and substantially eliminates the operator induced variability associated with subsequent Dose Determinations. In particular, the methods and apparatus describe herein provide a robotic automated cascade impactor that provides automation of the process of coupling the impactor stages together during delivery of a sample dose, as well as automation of collection of the drug sample from each impactor stage and cleaning each impactor stage.

In an example embodiment, the Automated Cascade Impactor utilizes an Extension Mechanism operable to couple to a plurality of Impactor Stages. The Extension Mechanism is operable to compress and separate Impactor Stages with the Impaction Plates of the plurality of Impactor Stages via automation. When just the impactor stages are compressed in an automated manner, the drug dose can be delivered into the impactor. Thereafter, the automated cascade impactor can automatically uncompress each impactor stage, leaving a space between each impactor stage. The plurality of Isolation Stages is operable to be automatically inserted between respective Impactor Stages when the Impactor Stages are separated by the Extension Mechanism. The plurality of Isolation Stages are then automatically compressed between Impactor Stages with the Impaction Plates to isolate each Impactor Stage from at least one adjacent Impactor Stage. The plurality of Isolation Stages is operable to be automatically uncompressed and removed from between the Impactor Stages.

In example embodiment disclosed herein, the Automated Cascade Impactor utilizes an extension mechanism that has impactor mounts that hold each impactor stage, and that move along an extension guide, ensuring true vertical motion.

In example embodiment disclosed herein, the Automated Cascade Impactor utilizes an extension actuator that collectively compresses Isolation Stages and Impactor Mounts (and hence the impactor stages), in a synchronized and symmetric manner, by means of being attached to succeeding linkages and the collective Extension Assembly actuated by an Extension Actuator. Three Extension Actuator guides are used, each spaced 120 degrees apart to provide uniform opening and closing of the Automated Cascade Impactor assembly. In one example embodiment disclosed herein, the Automated Cascade Impactor ensures deposition of particulate matter within each Impactor Stage and on each Impaction Plate.

In one example embodiment disclosed herein, the Automated Cascade Impactor applies a compressive force to insure complete sealing of Impactor stages with the Impaction Plate when injecting a drug through the Glass Entry port of a throat, and ensures sealing the Impactor Stages when the Isolation stages are inserted between impactor stages in the sample collection mode.

In an example embodiment disclosed herein, the Automated Andersen Cascade Impactor utilizes hydraulic, magnetic and/or electromechanical force to actuate the Extension Actuators and isolation actuator.

In an example embodiment disclosed herein, the Automated Cascade Impactor sandwiches the Isolation Stages between Impactor Stages with the Impaction Plates.

In example embodiment disclosed herein, the Automated Cascade Impactor injects and extracts fluids through Fluid Ducts in each Isolation Stage.

In example embodiment disclosed herein, the Automated Cascade Impactor utilizes an Oscillation Mechanism to agitate the Automated Cascade Impactor assembly in at least one of: a horizontal axis of rotation, a vertical axis of rotation, and a conical axis of rotation.

In example embodiment disclosed herein, the Automated Cascade Impactor comprises an entry throat that is exchangeable.

In an example embodiment disclosed herein, the Automated Cascade Impactor provides a mechanism that is easy and economical to manufacture, and operate.

In an example embodiment disclosed herein, the Automated Cascade Impactor sandwiches, between Impactor Stages, an imaging system that takes images of the orifices, so that the diameters of the orifices may be accurately measured.

In example embodiment disclosed herein, the Automated Andersen Impactor automates the determination of particle size distribution, using the Automated Cascade Impactor into which samples are injected. In one configuration, the impactor stages mounted within the impactor mounts are those of a conventional Andersen Cascade Impactor, thus producing an Automated Andersen Cascade Impactor. In the Automated Andersen Cascade Impactor, the length of the Automated Cascade Impactor column (when the extension mechanism compresses only the impactor stages) remains unaltered (as compared to a manual conventional impactor, such as an Andersen Cascade Impactor) for delivery of the sample into the Automated Andersen Cascade Impactor using an aerosolized inhalation device, or any other device for that matter. Thus, the flight time and the path of the particles inside the Automated Andersen Cascade Impactor remain unaltered. This negates the need to perform bridging studies (had the Andersen Column been altered) with respect to current data. For the same reason, comparison of particle size distribution with data associated with other studies remains the same (i.e., bridging studies are not required).

When preparing the samples (from the dose injected into the Automated Cascade Impactor while only the impactor stages are compressed), the Impactor Stages are then extended or separated by means of an Extension Mechanism(s), and the Extension Actuator as if they were bellows. Isolation Stages are then inserted and interleaved/sandwiched between the extended Andersen Impactor Stages and Andersen Impactor Impaction Plates (providing the interior surfaces upon which particular matter samples collect in each impactor stage). Then, the entire assembly is symmetrically closed (as a bellow is closed) or symmetrically compressed with the Extension Guides assuring true motion in the sense that Impactor Stages and the Isolation Stages sandwiched between them remain parallel and in alignment with each other. This ensures leak-proof closure when this assembly is closed and compressed.

Upon successful leak-proof closure, each impactor stage is completely isolated from the others. Solvents are injected into each Automated Impactor isolation Stage through valves mounted in the Isolation Stages. The Column Assembly is agitated and rotated or vibrated for a pre-determined time to dissolve the samples from each Andersen Impactor Stage and respective Impaction Plate. Using pumps, the samples are extracted through Fluid Ducts in the Isolation Stages and transferred into closed vials for chemical analysis.

After the solvents (extraction agents) have been pumped out, wash or cleaning solvents or agents are pumped in through valves mounted in the Automated Impactor Isolation Stages. The Automated Cascade Impactor is agitated as before, and the wash solvent is pumped out. This cycle is repeated for a pre-determined time. The stages are then dried using nitrogen as a drying agent, and the stages are uncompressed and extended. The interleaved isolation stages are pulled out and the Automated Cascade Impactor Column is closed (i.e. only the impactor stages are re-compressed). The closure is detected by electronically measuring the difference between the inlet and exit airflow through the Automated Cascade Impactor Column. If the difference between the airflows is within specifications, the Automated Andersen Cascade Impactor is ready for the next sample injection, then cleaning and drying. If the difference between the airflows is not within specifications, the software instructs the Extension Actuator to increase the closing force in graduated increments. If closure is still not detected, the software warns an operator of a system malfunction.

BRIEF DESCRIPTION OF THE DRAWINGS

FIG. 7 is a flow chart of processing operations performed by an Automated Cascade Impactor as disclosed herein.

DETAILED DESCRIPTION

Embodiments disclosed herein provide an Automated Cascade Impactor that allows multiple Dose Determinations per day in a manner that is much faster than manual operation of a conventional cascade impactor, and substantially eliminates the operator induced variability associated with the current and subsequent Dose Determinations.

Figure 1:
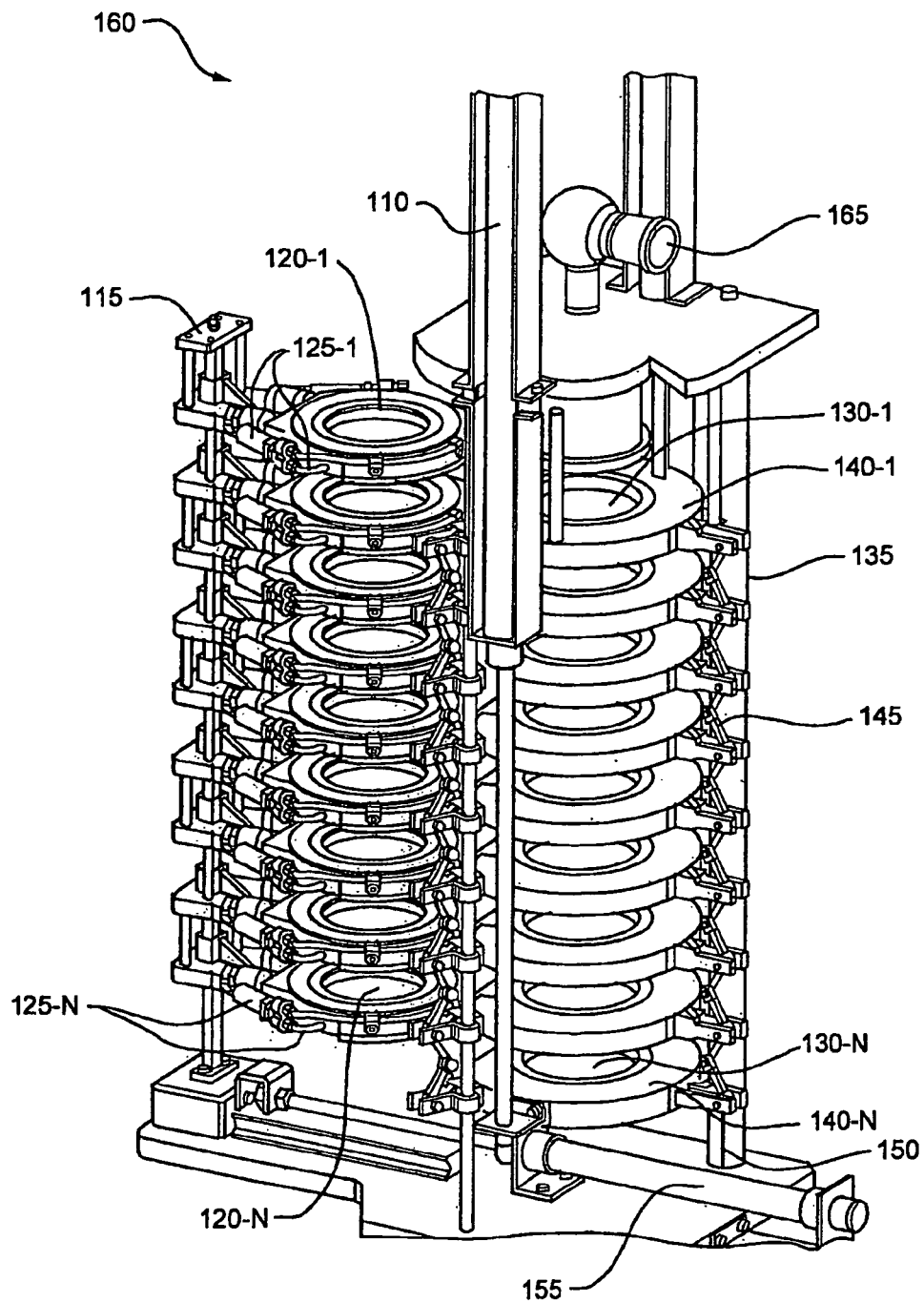
FIG. 1 illustrates a high level view of the Automated Cascade Impactor according to one embodiment disclosed herein.
Figure 2:
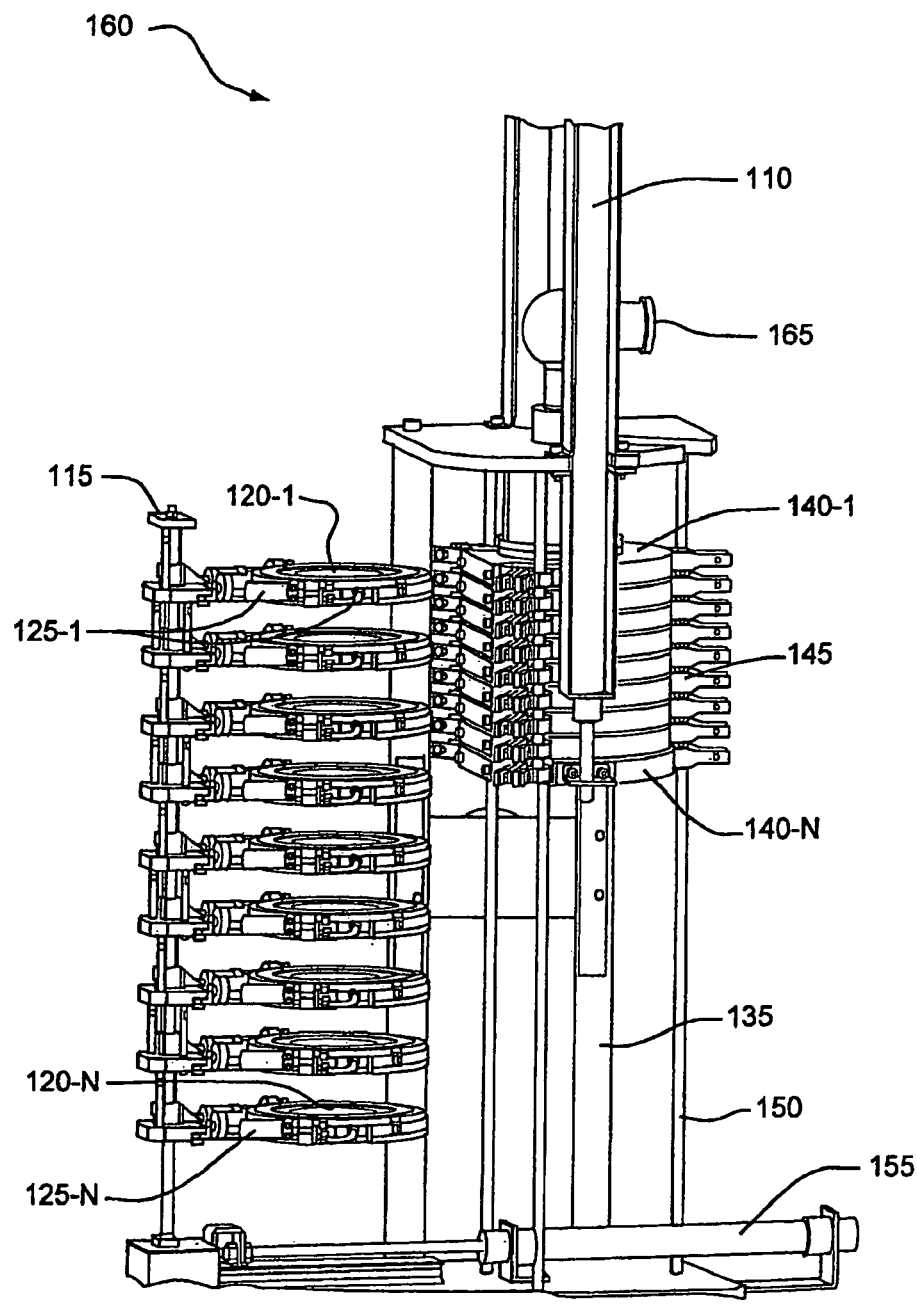
FIG. 2 illustrates a high level view of the Automated Cascade Impactor wherein the impactor stages are compressed, according to one embodiment disclosed herein.

FIG. 1 illustrates an example embodiment of the Automated Cascade Impactor 160 used to test Dose Determination via an entry throat 165 that is coupled (as will be shown in successive figures) to an uppermost impactor stage 130-1 during compression of the plurality of impactor stages 130-N. The entry throat 165 allows coupling of a delivery device, such as an inhaler (not shown), for dispensing of particulate matter such a drug particulates in an aerosol spray (through the entry throat 165 into the plurality of compressed impactor stages 130-N). In one example embodiment, the entry throat 165 is exchangeable. The Automated Cascade Impactor 160 further includes an extension mechanism 135 that is coupled to a plurality of impactor stages 130-N. The extension mechanism 135 is operable to compress and separate impactor stages 130-N, as required and as will be explained, via automation. Generally, the extension mechanism includes a linkage 145 that couples each impactor housing 140 (that mounts an impactor stage 130), the extension guides 150, and extension actuator 110. In particular, as will be shown and described in more detail in FIG. 2, the extension mechanism 135 is able to initially compress just the impactor stages 130-N to automatically configure the impactor stages 130-N in position with each other for administration of a dose regimen (a dose regimen can be one to many doses) of a drug from an inhaler device (not shown in figure) coupled to the throat 165. After administration of the drug particles to each compressed impactor stage 130, the extension mechanism 135 can uncompress the impactor stages 130-N to a position as shown in FIGS. 1 and 3 (i.e., providing a space between each impactor stage). Once the impactor stages have collected the drug sample (FIG. 2) and have been separated as shown in FIGS. 1 and 3), a plurality of isolation stages 120-N are operable (via suspension and alignment provided by an isolation armature 115) to be automatically inserted (via an operation of an isolation actuator 155) between respective impactor stages 130-N when the impactor stages 130-N are separated by the extension mechanism 135 (i.e., after the drug has been delivered to each stage for testing). This configuration is shown in FIG. 4. The plurality of isolation stages 120-N are then automatically compressed between impactor stages 130-N to isolate each impactor stage 130-1 from at least one adjacent impactor stage 130-1 as shown in FIG. 5. The compression is symmetric and the isolation stages 120 are able to vertically travel upward (e.g. slide) upon the isolation armature 155 (upon a hardened steel shaft) as each impactor stage 130 comes into contact with an adjacent isolation stage 120. In this fully compressed configuration, each impactor stage 130 is automatically precisely aligned and isolated from adjacent impactor stages via the insertion and symmetric compression of the intervening isolation stages 120. That is, the isolation stages 120 become sandwiched and aligned between the impactor stages 130 as shown in FIG. 5. Isolation stages 120 may also be referred to herein as separation stages. In the fully compressed configuration as shown in FIG. 5, the plurality of isolation stages 120-N each include fluid ducts 125 (that can include valves) that are operable to control and direct injection of collection fluid into each impactor stage to collect the particulate matter (i.e. the drug sample) that has been deposited onto interior surfaces of each impactor stage 130-1. The fluid ducts 125 and associated valves of each isolation stage 120 are also operable to inject cleaning and drying fluids into each isolated impactor stage 130 to clean and dry surfaces of the impactor stage 130. Entry ports of each fluid duct into the internal voids defined within each impaction stage can be positioned at an angle to provide a turbulent or whirlpool effect as the fluid enters and fills the internal area. This turbulence of the liquid extraction agent (used to collect the particulate matter drug sample) due to a direction of entry can assist in removing the material from internal surfaces such as an impactor plate within each impaction stages 130. Details of separation stage 120 flexible coupling 121 to the isolation armature 115 and access and placement of fluid ducts (and valves) 125 are shown in FIG. 10 for the reader's reference. The plurality of Flexible Couplings 121-N allows wiggle of the plurality of Isolation Stages 120-N so as to automatically align the Plurality of Isolation Stages 120-N when they are sandwiched and compressed between the plurality of Impactor Stages 130-N with the adjacent Impactor Stages 130-N above and below then, as described elsewhere in this document for sample preparation and cleaning, after the dose injection step.

In one configuration, as shown in detail in FIG. 9, each isolation stage 120 has an isolation housing 196 having an upper sealing edge 198 and a lower sealing edge (on the underside, not visible in FIG. 9). The isolation housing 196 is sized proportionately to a diameter of an impactor stage 130 (that may include an impactor plate) of a cascade impactor (such as an Andersen cascade impactor stage) such that at least one of the upper sealing edge 198 and lower sealing edge can be compressed to at least one sealing edge 132 of an adjacent impactor stage 130 to isolate an internal volume 136 of the adjacent impactor stage when the stages 120 and 130 are compressed against each other. The fluid duct(s) 125 (of which there are two per isolation stage 120 in the example shown in FIG. 9) passing through the isolation housing 196 allow fluid communication with the isolated internal volume 136 of the adjacent impactor stage 130 for particulate matter drug sample extraction, cleaning and drying on interior surfaces of that impactor stage 130 (such interior surfaces include an impactor plate of that impactor stage).

FIG. 2 illustrates an example embodiment of the Automated Andersen Cascade Impactor 160 when the extension mechanism 135 symmetrically compresses just the impactor stages 130-N via automation. An entry throat 165 is coupled to an uppermost impactor stage 130-1 during compression of the plurality of impactor stages 130-N. The extension mechanism 135 includes a coupling to a plurality of impactor mounts 140-N. Each impactor mount 140-1 is coupled to a respective impactor stage 130-1 of the plurality of impactor stages 130-N. The impactor stages 130 can be those of a conventional cascade impactor, such as an Andersen Cascade Impactor. The impactor stages 130 for purposes of this description can refer to the impactor mounts 140 as well as the Andersen cascade impactor stage or housing mounted therein. Each impactor mount 140-1 includes a linkage 145 that couples that impactor mount 140-1 to at least one adjacent impactor mount 140-2, and allows the extension mechanism 135 to compress and separate adjacent impactor stages 130-N in an automated manner as required during different phases of operation of the impactor 160. Refer to FIG. 8 for a detailed view of the linkage 145 as it relates to impactor stages 130. The plurality of isolation stages 120-N, each including fluid ducts 125, are coupled to an isolation armature 115 that includes the isolation actuator 155 and are positioned off the side while just the impactor stages 130 are compressed. Thus, FIG. 2 represents a phase of configuration of the impactor 160 during which a dose of a drug may be delivered into the entry throat 165 for deposition of drug particulate matter on that dose onto interior surfaces of each impactor stage 130 (including surfaces of an Impaction Plate within that stage).

In an example embodiment, the extension mechanism 135 includes at least one extension guide 150 upon which each impactor mount 140-1 travels during compression and separation of impactor stages 130-N. The extension guides 150 causes the plurality of impactor mounts 140-N and respectively coupled impactor stages 130-N to be vertically aligned during compression and separation. In the illustrated design, there are three extension guides 150 arranged in a triangular and symmetric configuration and each impactor mount 140 is able to slide up and down the extension guides 150 under guidance from the extension mechanism linkage 145 as the extension actuator 110 raises the lowermost impactor housing or mount 140-N (that mounts the lowermost impactor stage 130).

In an example embodiment, the extension actuator 110 is coupled to the extension mechanism 135 and can symmetrically compress the impactor stages 130 alone (as shown in FIG. 2), and can symmetrically separate the impactor stages 130 making room for insertion of the isolation stages 120 in between each impactor stage 130, and can then operate to symmetrically compress (and uncompress) the collection of alternating impactor stages 130 and isolation stages 120. The extension actuator 110 is thus operable to provide compressive force to the extension mechanism 135. The compressive force collectively compresses the impactor mounts 140-N of the extension mechanism 135 towards each other in a sandwiching effect. The impactor mounts 140 maintain alignment with each other via linkage mechanisms 145 (of which there are three spaced symmetrically around the perimeter of the impactor mounts 140) that can slide up and down (under control of the extension actuator 110) upon the extension guides 150. This causes automatic alignment as well as compression of each impactor stage 130-1 (mounted within each impactor mount 140) to an adjacent impactor stage 130-2 during operation of the Automated Cascade Impactor 160 for the purpose of sample preparation (i.e. drug dose delivery) and collection.

In an example embodiment, the extension actuator 110 is operable to provide the compressive force via the extension mechanism 135 to each impactor stage 130-1 to seal each impactor stage together in preparation for dose delivery. In one configuration, the compressive force is applied in an increasing manner until seals formed between boundaries of each impactor stage 130-1 (compressed against the next impactor stage 130) are sufficient to maintain a predetermined gas pressure applied to an internal volume defined by internal areas of the collectively compressed impactor stages 130-N. In an example embodiment, the extension actuator 110 is pneumatically operated, or electrically operated or may be electro-mechanically or magnetically operated. Once the impactor stages 130 are compressed as shown in FIG. 2, a dose of drug may be delivered via the entry throat 165 while the predetermined air flow pressure remains applied to an internal volume defined by the collectively compressed impactor stages 130-N. This air flow may be caused by drawing suction from the lowermost impactor stage 130-N, thus simulating inhalation by a person's lung. As the drug is delivered, particulate matter settles or impacts onto interior surfaces of each compressed impactor stage 130 and onto Impaction Plates in those stages. After drug delivery is complete, the air flow is stopped and it is now time for the automated cascade impactor 160 to perform the phase of sample preparation and sample collection. This entails separating each impactor stage 130 and inserting there-between a respective isolation stage 120 to automatically collect the drug sample from a given impactor stage 130, as well as clean and dry interior surfaces of that impactor stage 130 in preparation for delivery of the next drug sample. This process can be repeated many times faster than a conventional cascade impactor operated in a manual manner by a human. As an example, a human can manually operate a conventional Andersen Cascade Impactor to perform two dose deliveries (and extractions and cleanings) in a 7-8 hour period of time, whereas the system disclosed herein can deliver, extract and clean the cascade impactor in approximately one hour.

Figure 3:
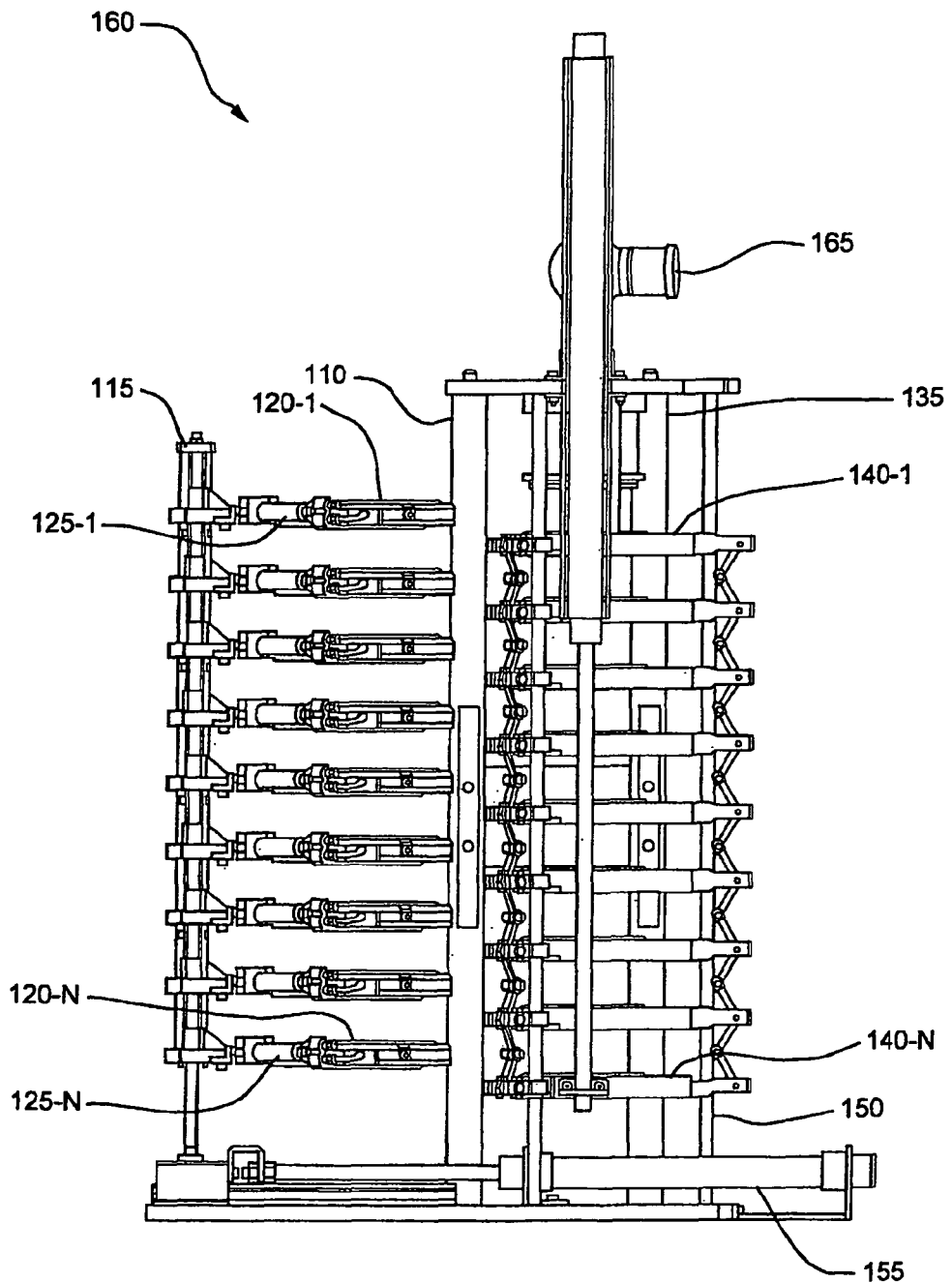
FIG. 3 illustrates a high level view of the Automated Cascade Impactor wherein the impactor stages are uncompressed, according to one embodiment disclosed herein.

FIG. 3 illustrates an example embodiment of the Automated Cascade Impactor 160 after drug delivery, but prior to insertion of the isolation stages 120. In this example embodiment, the extension actuator 110 is operable to release compressive force applied to the extension mechanism 135 to collectively separate and lower the impactor mounts 140-N of the extension mechanism 135 down away from each other, causing separation of each impactor stage 130-1 from an adjacent impactor stage 130-2 after deposition of particulate matter (i.e. drug sample delivery) within each impactor stage 130-1.

Once the impactor stages 130 are fully uncompressed and separated, the plurality of isolation stages 120-N are operable to be automatically inserted between respective impactor stages 130-N (i.e. after the extension actuator 110 operates to separate the impactor mounts 140-N and impactor stages 130 away from each other by lowering the lowermost impactor stage 130-N). During lowering of the lowermost impactor stage 130-N, the linkage mechanisms 145 coupling each impactor mount 140 maintain alignment of each stage 130 and also control the vertical spacing and stop location or placement of each stage once the lowermost stage is fully lowered. Thus the separation of each impactor stage 130-1 from an adjacent impactor stage 130-2 takes place after deposition of particulate matter within each impactor stage 130-1 and when fully separated, each impactor stage 130 is spaced apart from one another allowing enough room for insertion of the isolation stages 120.

As further shown in FIG. 3, a plurality of isolation stages 120-N, including fluid ducts 125-N, are coupled to an isolation armature 115 that includes an isolation actuator 155. The isolation actuator 155 may be, for example, a hydraulic, mechanical or electric piston or servo that provides horizontal movement of the isolation armature 115 upon which each isolation stage 120 is mounted. The isolation actuator 155 and armature 115, and Flexible Coupling 121 thus provide concurrent insertion and alignment of each isolation stage 120 (mounted on the isolation armature 115) with at least one respective impactor stage 130 during automatic insertion of the isolation stages 120 between impactor stages 130.

Figure 4:
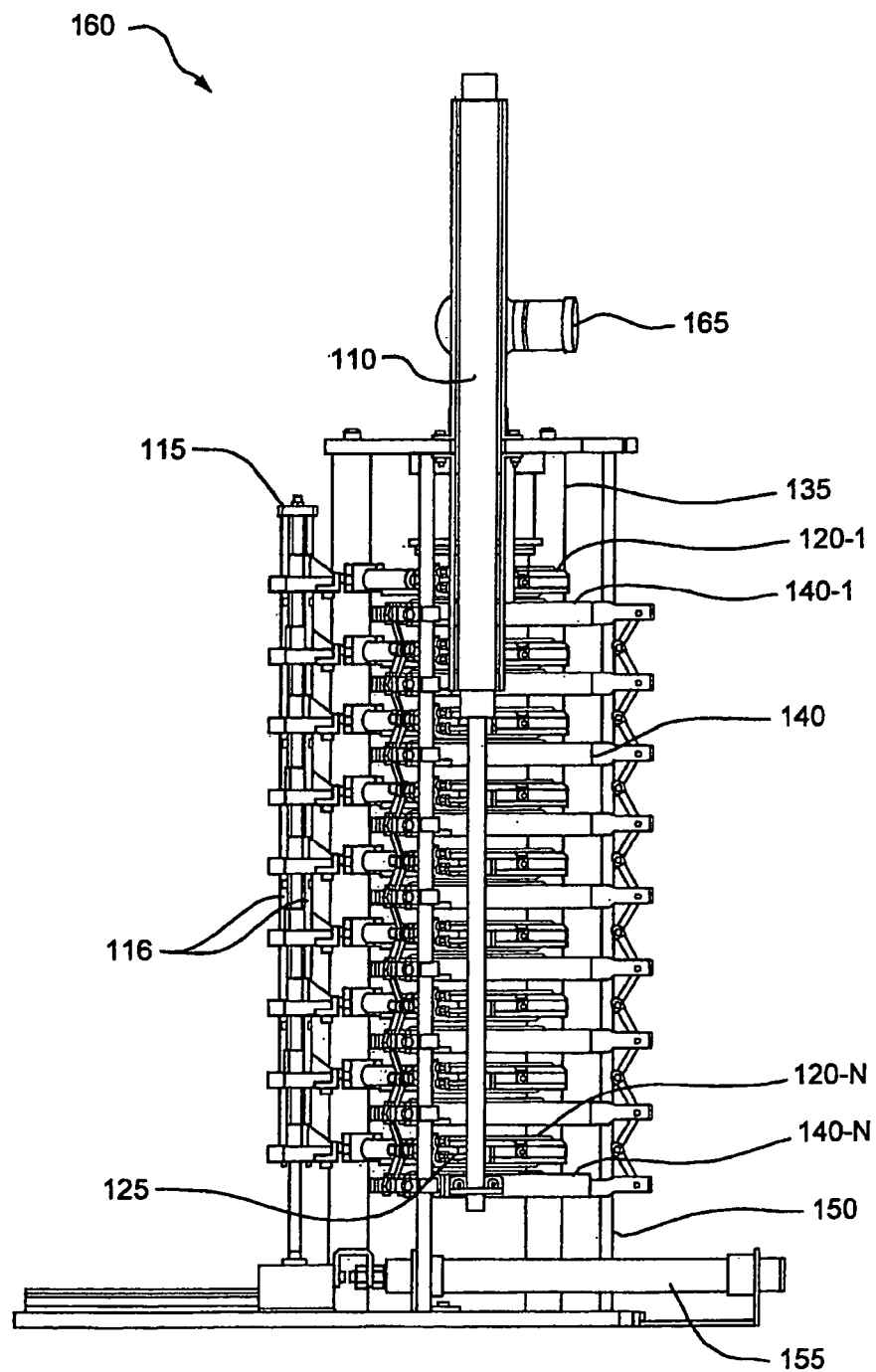
FIG. 4 illustrates a high level view of the Automated Cascade Impactor wherein the extension mechanism couples each impactor stage, and allows each impactor stage to be coupled with at least one adjacent impactor stage, according to one embodiment disclosed herein.
Figure 10:
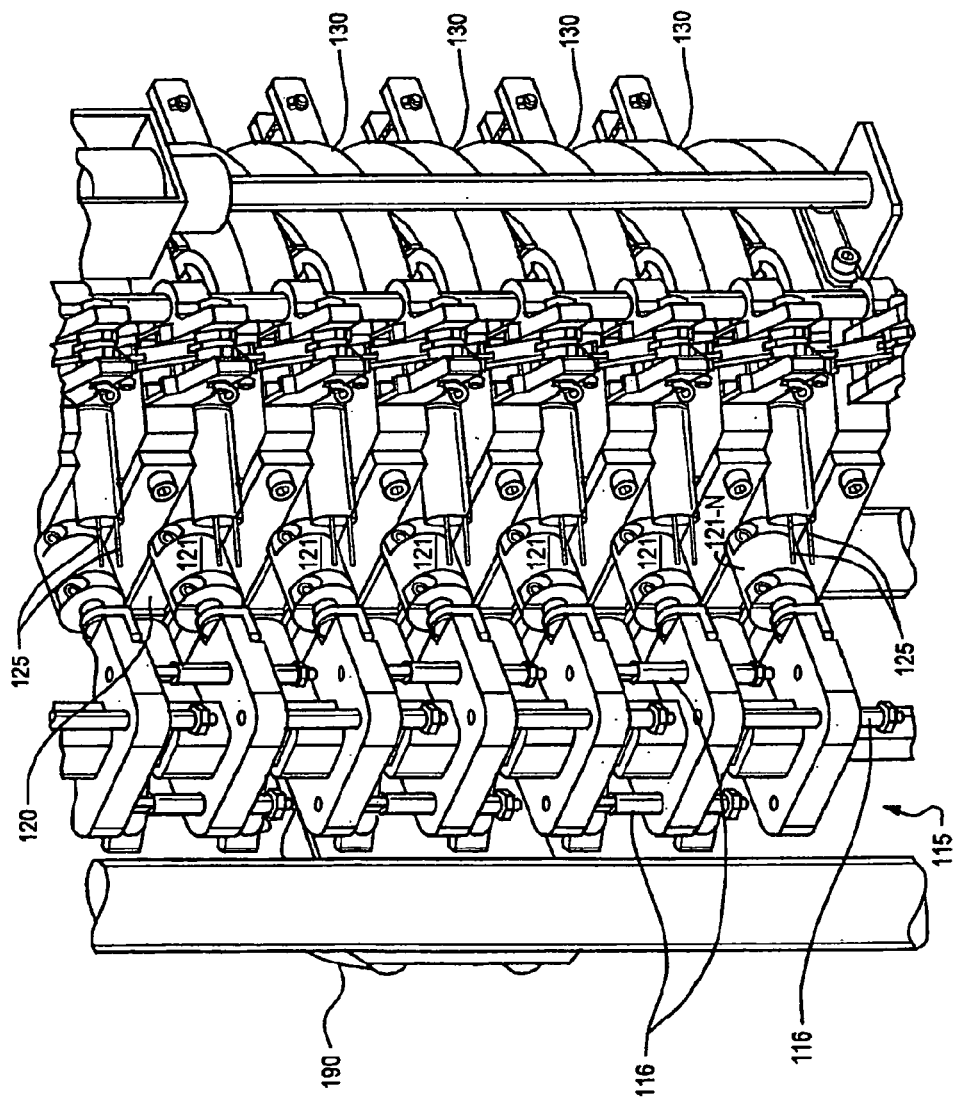
FIG. 10 shows details of separation stages as disclosed herein.

FIG. 4 shows the set of isolation stages 120 that are inserted and aligned with the set of impactor stage 130 via operation of the isolation armature 115 and the isolation actuator 155. In this configuration, the two sets of alternating isolation and impactor stages 120/130 can be compressed together. Note that the isolation armature 115 allows vertical travel of each isolation stage 120 upon the isolation armature 115 during both upward symmetric compression and downward symmetric separation of respective isolation stages 120 with impactor stages 130. Upon insertion and alignment of the isolation stages 120 between respective impactor stages 130, operation of the extension mechanism 110 allows the isolation stages to freely travel between, and symmetrically compress with, impactor stages via connection to the isolation armature to allow collective compression and alignment of the impactor stages and isolation stages. The isolation armature 115 includes isolation stage stops 116 that, during separation of respective isolation stages 120 with impactor stages 130, cause each isolation stage 120 to stop downward vertical travel at a predetermined location or stop position relative to at least one adjacent impaction stage 130. Details of the isolation stage stops 116 can be seen in FIG. 10 as well. In the illustrated configurations then, the isolation stages 120 do not require a separate vertical drive system from the impactor stages 130, but rather, simply maintain vertical alignment and spacing from each other via the isolation armature 115 and associated isolation stage stops 116. During compression, the isolation stages may travel and slide freely upward on the isolation armature and the extension actuator raises the lowermost impactor stage 130, thus picking up each isolation stage 120 as a lower impactor stage 130 comes into contact with the isolation stage 120 located above. During compression then, a sandwiching effect occurs from the bottom up of alternating impactor and isolation stages 130, 120.

In the configuration shown in FIG. 4, the extension actuator 110 operates to provide compressive force (via the extension mechanism 135) to the plurality of impactor stages 130-N and isolation stages 120-N inserted between respective impactor stages 130-N. The symmetric compressive force causes a sandwiching effect between alternating and aligned isolation and impactor stages that results in isolation of an internal volume of each impactor stage 130-1 from at least one adjacent impactor stage 130-2 to create separately isolated impactor stages 130-N.

Figure 5:
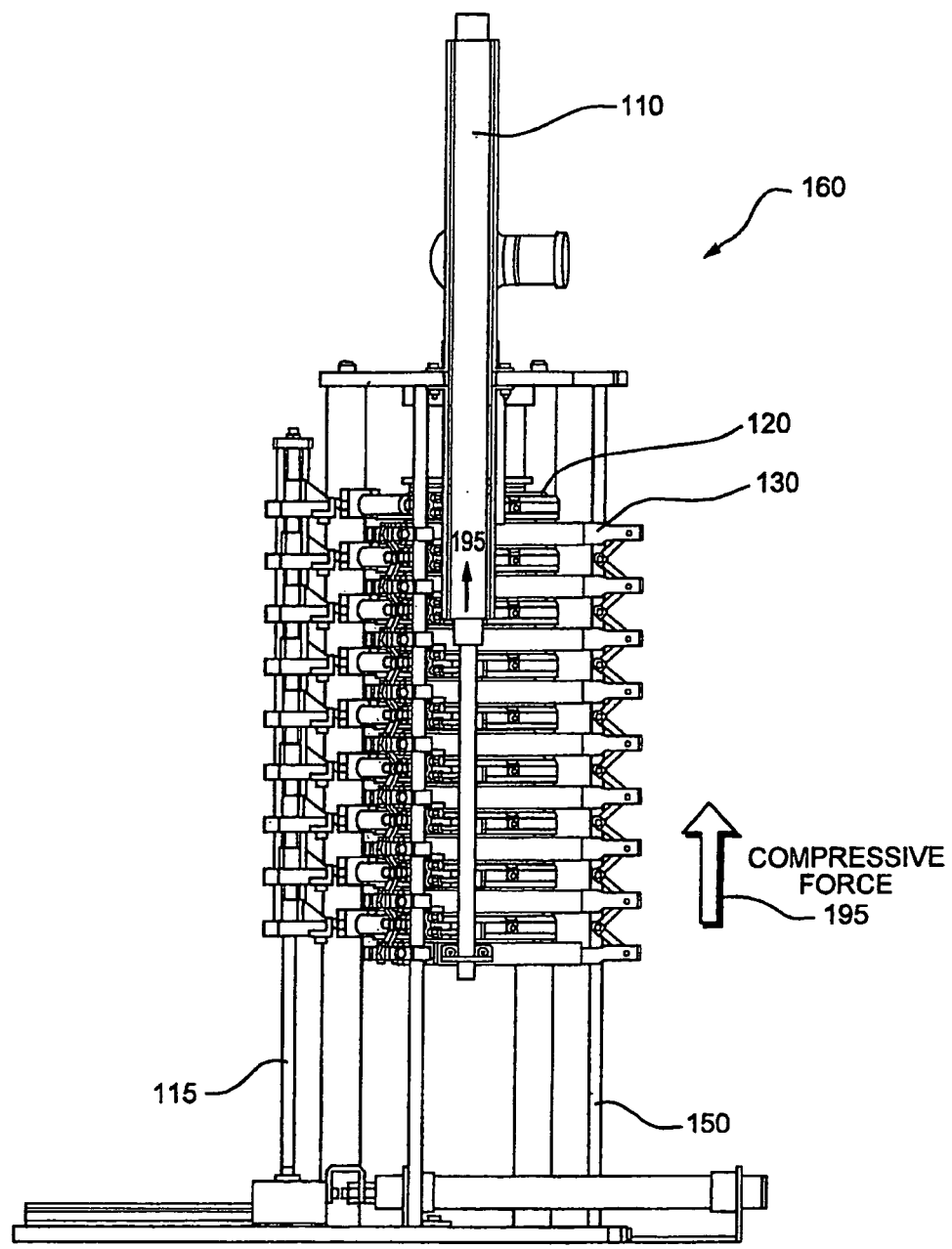
FIG. 5 illustrates a view of the Automated Cascade Impactor when all impactor and isolation stages are aligned and in a compressed state.
Figure 6:
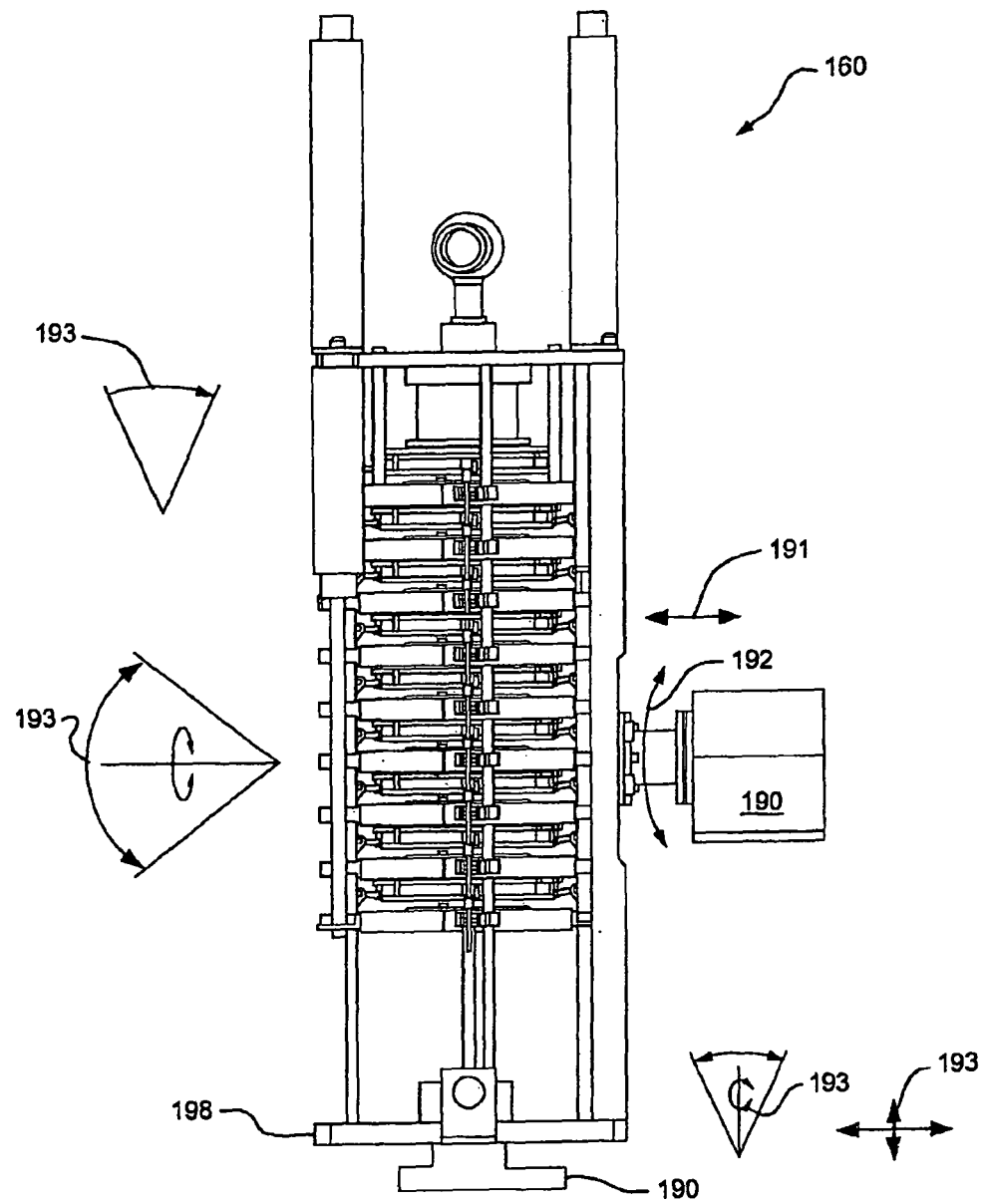
FIG. 6 illustrates agitation of the Automated Cascade Impactor from a side or bottom using various agitation patterns such as vibration, shaking, rotation (vertical, horizontal, conical) and the like to assist in extraction of the particulate matter sample from the interior surfaces of each stage.
Figure 8:
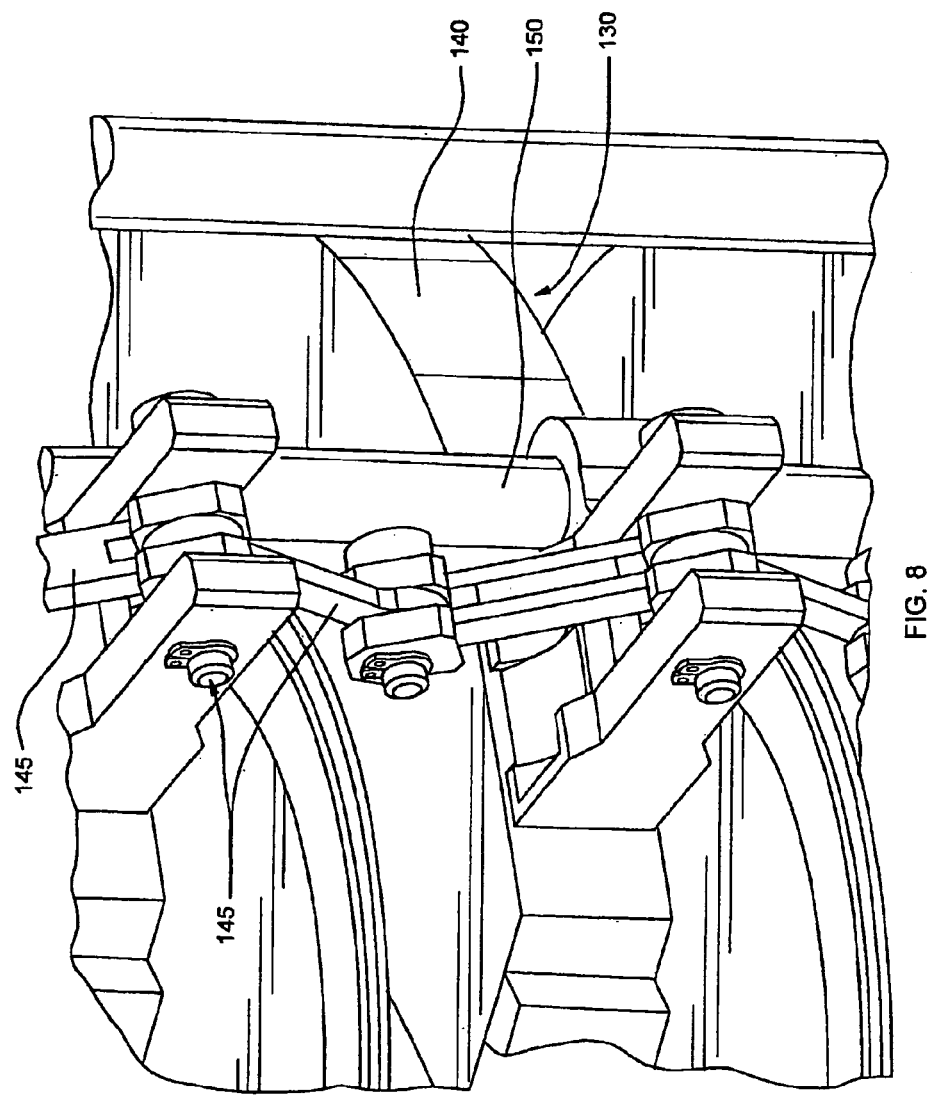
FIG. 8 shows details of an extension linkage as disclosed herein.
Figure 9:
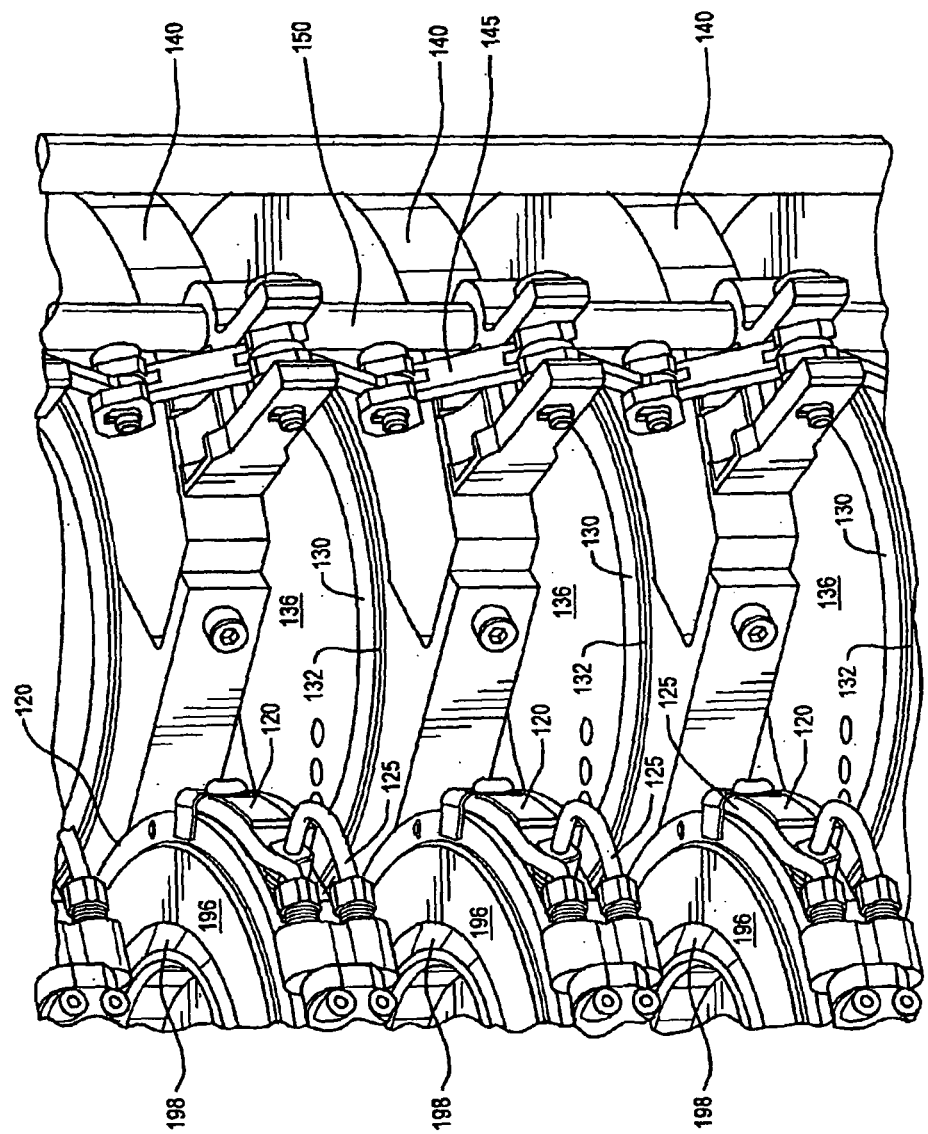
FIG. 9 shows details of separation stages and extension linkages as disclosed herein.

FIG. 5 shows the resultant configuration when the isolation stages 120 have been inserted and compressed with impactor stages 130 using compressive force 195 applied by the extension actuator 110 to all stages 120, 130. This configuration ensures a leak-proof closure as the interleaved or overlapping stages 120 and 130 are compressed. The leak-proof closure is detected by electronically measuring the difference between an inlet and exit airflow through the Automated Cascade Impactor Column of compressed stages (e.g., air flow differential between the uppermost stage and lowermost stage within specified limits). If the difference between the airflows is within specifications, the Automated Andersen Cascade Impactor is ready for extraction of the sample, then cleaning and drying. If the difference between the airflows is not within specifications, software controlling operation of the impactor 160 instructs the Extension Actuator 110 to increase the closing force 195 in graduated increments. If closure is still not detected, the software warns an operator of a system malfunction. Since the isolation stages 120 "float" on the isolation armature 115, they are able to rise and fall with the movement of the impactor stages being compressed of released up or down, and yet remain aligned.

In this compressed configuration as shown in FIG. 5, each isolation stage 120 is able to operate to extract the particulate matter drug sample delivered onto interior surfaces of a respective impactor stage 130. To do so, each isolation stage 120 includes at least one fluid duct 125-1 allowing fluid communication with the now-isolated internal volume of a respective impactor stage 130-1. Though not shown in the figures, flexible tubes may be attached to the fluid ducts 125 to supply and remove such fluid. In one example embodiment, at least one fluid duct 125-1 of each isolation stage 120 is operable to supply and extract a fluid collection agent to the internal volume of a respective impactor stage 130-1. This enables suspension and extraction, within the fluid collection agent, of the particulate matter (e.g. drug sample particles delivered via the sample dose when the impactor 160 was configured as shown in FIG. 2) disposed on internal surfaces of that isolated impactor stage 130-1. This drug collection process allows the automated cascade impactor 160 to accurately collect, remove and clean a drug sample separately from each impactor stage 130 without human involvement.

After drug collection is complete using the extraction agent fluid, at least one fluid duct 125-1 of each isolation stage 120-1 is operable to supply a fluid cleaning agent to the internal volume of a respective impactor stage 130-1 to enable cleaning of that isolated impactor stage 130-1. Additionally, at least one fluid duct 125-1 of each isolation stage 120 is operable to supply a fluid drying agent (a liquid or gas) to the internal volume of a respective impactor stage 130-1 to enable drying of internal surfaces of that isolated impactor stage 130-1. The fluid cleaning agents and drying agents may be liquids or gases of a type known to those skilled in the art.

FIG. 6 shows an example embodiment that includes an oscillation mechanism 190 is coupled to the Automated Cascade Impactor 160. The oscillation mechanism 190 is a motor, servo or other motion inducing mechanism that provides movement 191, 192, 193 (e.g. rotation, shaking, vibration, etc.) of at least a portion or all of the Automated Andersen Cascade Impactor 160 after at least one fluid duct 125-1 of each isolation stage 120-1 is operated to provide either the fluid collection, cleaning and/or drying agent. Note the oscillation mechanism may be coupled to a side portion of the assembly 160 or may be coupled to a bottom portion as shown in FIG. 6. It will be appreciated that coupling the oscillation mechanism 190 to other areas of the automated cascade impactor 160 would work as well to enable oscillation or shaking of the assembly 160 to assist in drug extraction and cleaning of the system. As noted above, the fluid duct 125-1 is operated to supply the fluid collection agent to the internal volume of a respective isolated impactor stage 130-1. As an example, before full extraction of the fluid collection agent, the movement of the Automated Cascade Impactor 160 from the oscillation mechanism causes agitation of the fluid collection agent for displacement of the particulate matter disposed on internal surfaces of each isolated impactor stage 130-1.

In an example embodiment, the oscillation mechanism 190 is operable to rotate the isolated impactor stages 130-N about at least one of a horizontal axis of rotation 192, a vertical axis of rotation 191, and/or a horizontal or vertical conical axis of rotation 193, or a random axis of rotation. It is to be understood that while the figures shows an oscillation mechanism 190 coupled to a side and/or base 198 of the assembly, other embodiments allow vibration of the entire impactor 160 and in such cases, the oscillation mechanism 190 can be affixed to other areas such as to a top portion, or to any suitable mounting point that is structurally sound. In a configuration attached to the bottom portion, the agitation or shaking pattern can be conical or orbital such that the collective set of compressed impactor stages and separation stages can be oscillated in a conical or circular or orbital manner. It is also to be understood that variations in oscillation speed and timing and motion can be utilized to best cause the particulate matter to be removed from interior surfaces and suspended in a liquid agent used for extraction. After cleaning, the extension mechanism 110 can operate to lower the lowermost impactor stage 130, causing each isolation stage 120 to begin sliding downward along the isolation armature 115. As noted above, the isolation armature includes isolation stage stops 116 (shown in FIGS. 4 and 10, that, during separation of respective isolation stages with impactor stages, cause each isolation stage 130 to stop downward vertical travel at a predetermined location relative to at least one adjacent impaction stage. Once uncompressing of the impactor stages 130 and isolation stages 120 is complete, the isolation actuator 155 can be operated to move the isolation armature 115 and attached isolation stages 120 from between the impactor stages 120.

FIG. 7 shows method steps performed when operating an automated cascade impactor as described herein.

In step 200, the automated cascade impactor 160 automatically (and symmetrically) compresses together a plurality of impactor stages 120 of the automated cascade impactor as shown in FIG. 2. During this process, the impactor 160 can measure a pressure of an internal volume defined within the compressed stages to determine when compression force is sufficient to form an appropriate seal between the compressed stages 120 and 130.

Next, in step 201, automated cascade impactor 160 receives particulate matter dispensed into the plurality of impactor stages 120 while they are compressed.

In step 202, the automated cascade impactor 160 automatically separates the plurality of impactor stages 120 as shown in FIGS. 1 and 3.

In step 203, the automated cascade impactor 160 automatically inserts (and maintains alignment of) a plurality of isolation stages 120 between impactor stages 130 as shown in FIG. 4.

In step 204, the automated cascade impactor 160 automatically and symmetrically compresses (and maintains alignment of) the impactor stages 130 and inserted isolation stages 120 to isolate each impactor stage 130 from at least one adjacent impactor stage 130, as shown in FIG. 5.

In step 205, the automated cascade impactor 160 supplies a fluid collection agent, via each isolation stage 120, to the internal volume of a respective impactor stage 130 to enable dissolution, suspension and extraction, within the fluid collection agent, of the particulate matter disposed on internal surfaces of that isolated impactor stage. During or after presentation of the fluid collection agent via ducts 125 (and associated valves) the oscillation mechanism 190 can be used to shake and agitate the fluid collection agent to aid in removing particulate matter from all internal surfaces of the impactor stages upon which the material may have been deposited (including the impactor plates of each impactor stage). The amount or volume of fluid collection agent can be a measured or pre-calculated amount. After the shaking, fluid samples of dissolved drug are collected by operation of pumps through the fluid ducts 125 (and associated valves) attached to each of the isolation stages 120.

In step 206, the automated cascade impactor 160 supplies and thereafter extracts a fluid cleaning agent (through ducts and associated valves 125), via each isolation stage 120, into the internal volume of a respective impactor stage 130 to enable cleaning of that isolated impactor stage. The oscillation mechanism 190 can also be used after supplying the cleaning agent, but before extraction, to assist in the cleaning process by agitating the assembly to cause the cleaning agent to thoroughly clean interior surfaces. After agitation, the cleaning agent can be extracted via suction applied to the fluid ducts 125 (via valve control).

In step 207, the automated cascade impactor 160 supplies a fluid drying agent to the internal volume of a respective isolated impactor stage 130 to enable drying of internal surfaces of that isolated impactor stage. The drying agent may be in a gas or liquid state applied via fluid ducts 125 under high or low pressure.

As noted above, during steps 205, 206 and 207, the impactor 160 can operate an oscillation mechanism 190 to provide movement of at least a portion of the automated cascade impactor, for example after supplying the fluid collection agent to the internal volume of a respective isolated impactor stage, and before full extraction of the fluid collection agent. The movement of the impactor 160 from the oscillation mechanism 190 causes agitation of the fluid collection agent for displacement and extraction of the particulate matter disposed on internal surfaces of each isolated impactor stage. In this manner, substantially complete extraction is obtained. Oscillation can be used during cleaning and drying cycles as well.

Figure 11:
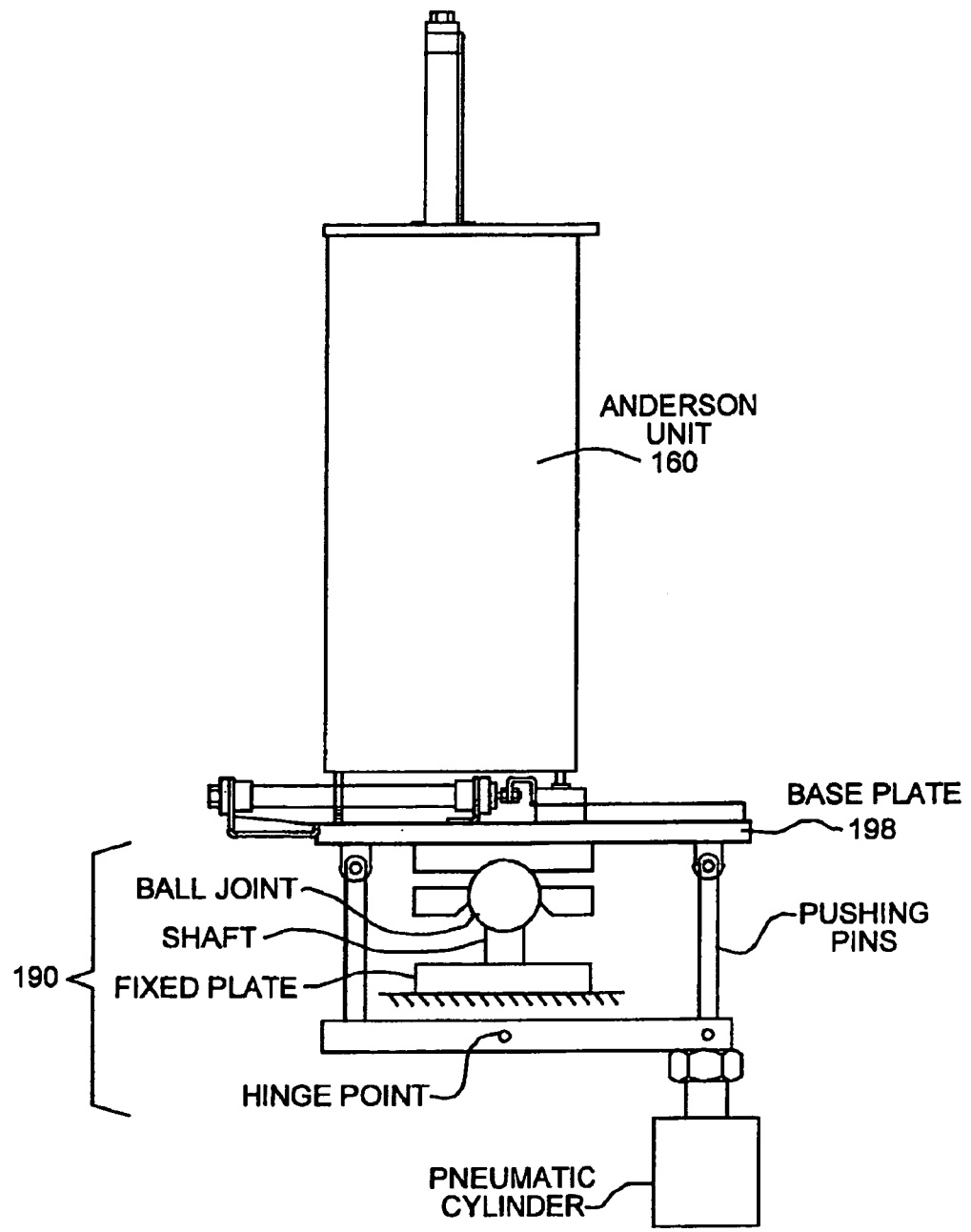
FIG. 11 shows a pneumatic cylinder and ball joint mechanism operating as an oscillation mechanism.
Figure 12:
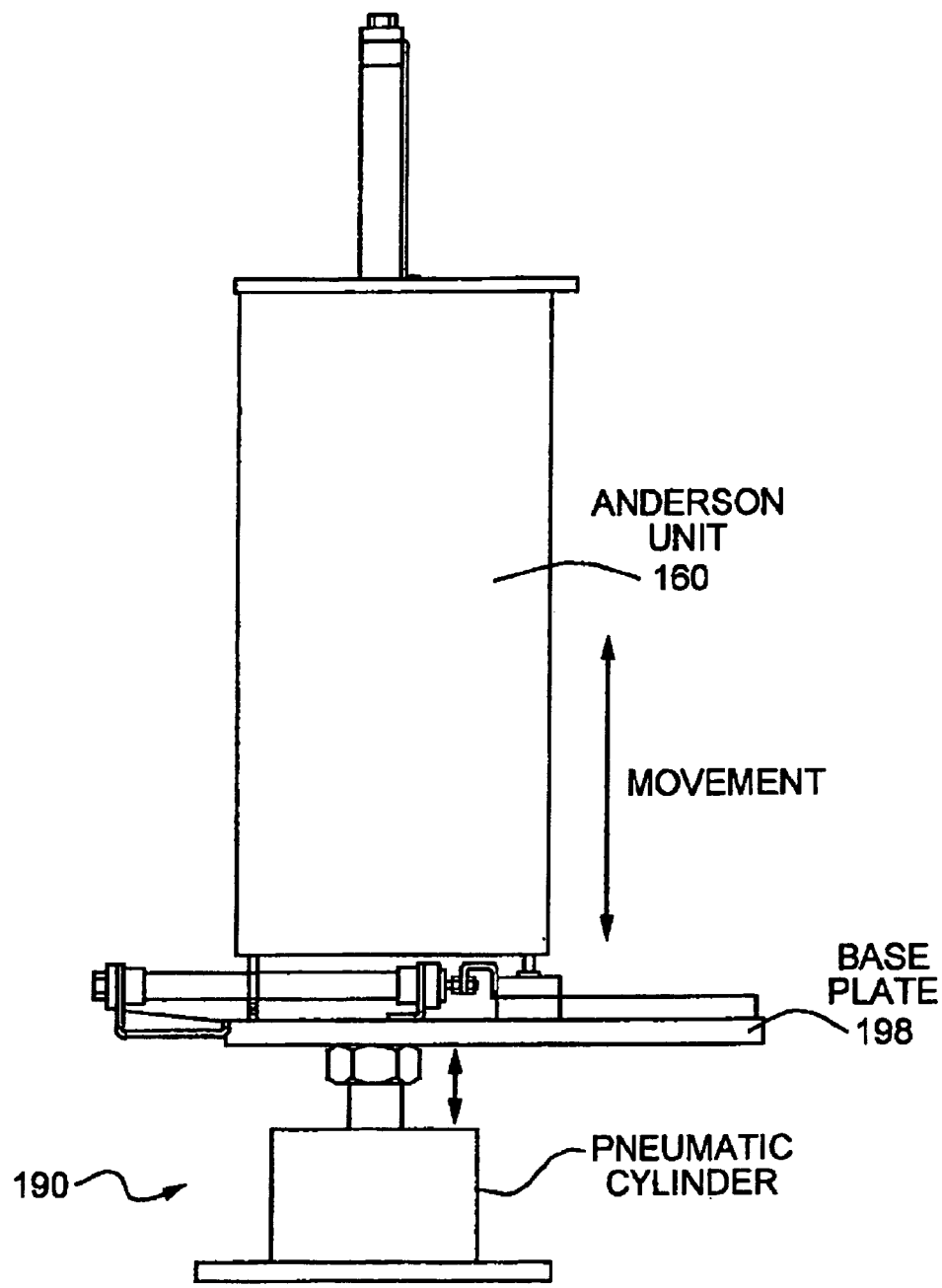
FIG. 12 shows a pneumatic cylinder operating as an oscillation mechanism.
Figure 13:
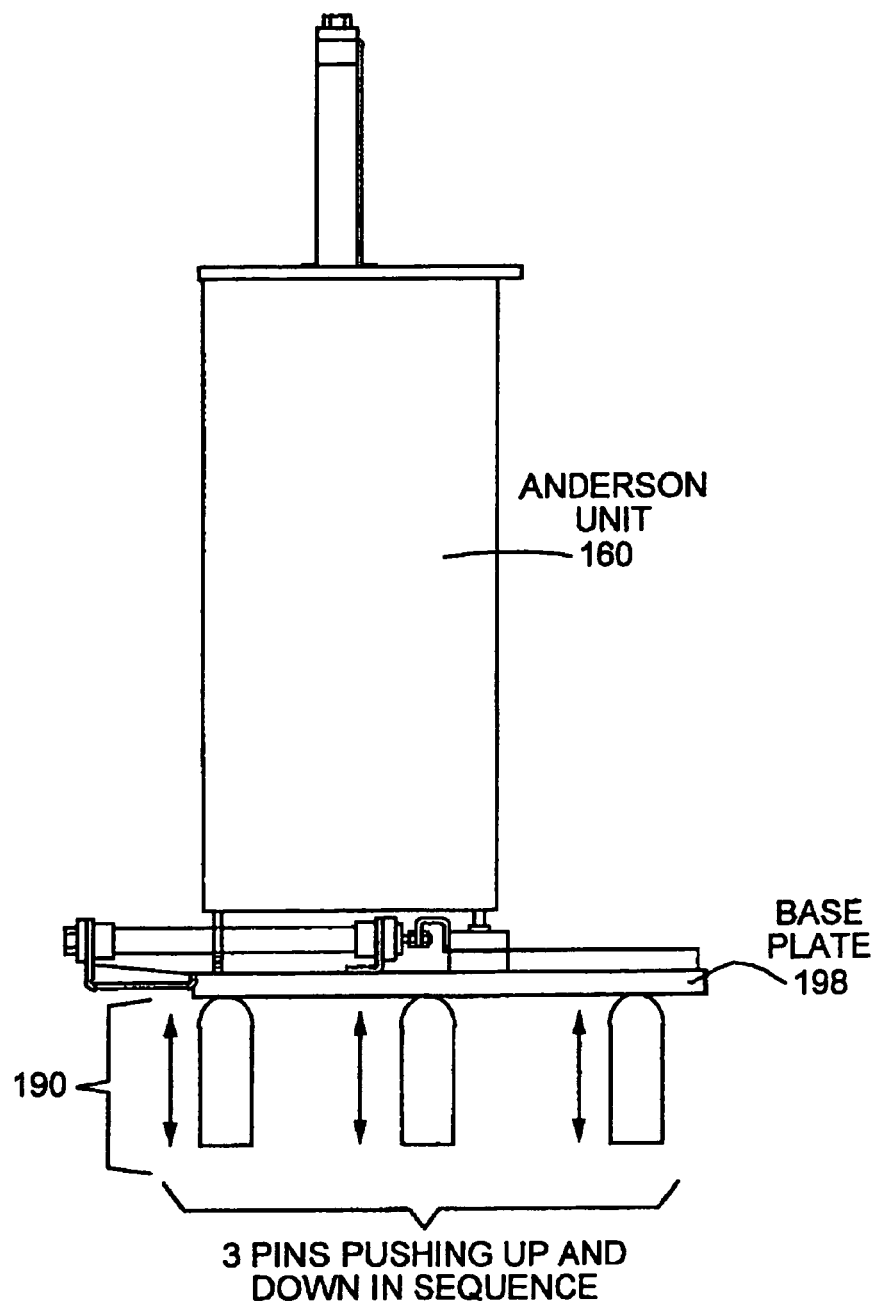
FIG. 13 shows a push pin mechanism operating as an oscillation mechanism.

FIGS. 11, 12 and 13 show example variations of the oscillation mechanism 190. In FIG. 11, the oscillation mechanism 190 is a pneumatic cylinder and ball joint mechanism. In FIG. 12 the oscillation mechanism 190 is a pneumatic cylinder and in FIG. 13 the oscillation mechanism 190 is a push pin mechanism.

In step 208, the automated cascade impactor 160 uncompresses and separates isolation stages 120 and impactor stages 130, and removes the isolation stages 120 from between impactor stages 130 thus returning the configuration to that shown in FIGS. 1 and 3.

Processing then repeats back to step 200 for a new drug dose sample to be delivered to the impactor and tested. Due to the automation of this entire process, sample doses can be collected at approximately one sample per hour as opposed to only two samples per day when performed manually using a conventional cascade impactor.

While configurations of the system and method have been particularly shown and described with references to configurations thereof, it will be understood by those skilled in the art that various changes in form and details may be made therein without departing from the scope of the invention. As an example, more of less impactor and separator stages 130, 120 can be used as may be needed for particular sample testing. Accordingly, the present invention is not intended to be limited by the example configurations provided above.

What is claimed is:

1. An automated cascade impactor, comprising:
a vertical array of a plurality of impactor stages;
an extension actuator operatively connected to at least one of said plurality of impactor stages so as to permit all of said plurality of impactor stages to move vertically away from each other such that all of said plurality of impactor stages are disposed in separated states with respect to each other, and to cause said plurality of impactor stages to move vertically toward each other such that all of said plurality of impactor stages are disposed in compressed states with respect to each other;
a vertical array of a plurality of isolation stages; and
an isolation actuator operatively connected to all of said plurality of isolation stages so as to respectively insert all of said plurality of isolation stages into spaces respectively defined between all of said plurality of impactor stages, and to respectively remove all of said plurality of isolation stages out from said spaces respectively defined between all of said plurality of impactor stages, when all of said plurality of impactor stages are disposed in said separated states with respect to each other, and to be respectively compressed between all of said plurality of impactor stages when all of said plurality of impactor stages are disposed in said compressed states with respect to each other whereby all of said plurality of isolation stages can isolate all of said plurality of impactor stages from each other.

2. The automated cascade impactor as set forth in claim 1, wherein:
said extension actuator is operatively connected to the lowermost one of said plurality of impactor stages.

3. The automated cascade impactor as set forth in claim 2, wherein:
said extension actuator is powered by a power source which is selected from the group comprising a pneumatic actuator, an electrical actuator, and electro-mechanical actuator, an electro-magnetic actuator, and a magnetic actuator.

4. The automated cascade impactor as set forth in claim 1, wherein:
said isolation actuator operatively connected to all of said plurality of isolation stages so as to respectively move all of said plurality of isolation stages in a horizontal mode such that all of said plurality of isolation stages can be inserted into all of said plurality of spaces respectively defined between all of said plurality of impactor stages, and to respectively move all of said plurality of isolation stages in a horizontal mode, out from all of said plurality of spaces respectively defined between all of said plurality of impactor stages, when all of said plurality of impactor stages are disposed in said separated states with respect to each other.

5. The automated cascade impactor as set forth in claim 4, wherein:
said isolation actuator is powered by a power source which is selected from the group comprising a hydraulic actuator, a mechanical actuator, an electrical actuator.

6. The automated cascade impactor as set forth in claim 2, wherein:
all of said plurality of impactor stages are interconnected to each other by a plurality of linkage mechanisms.

7. The automated cascade impactor as set forth in claim 6, wherein:
each one of said plurality of linkage mechanisms is respectively connected to each one of said plurality of impactor stages and is mounted upon at least one vertically oriented extension guide for slidably moving along said extension guide as said plurality of impactor stages move between said separated states and said compressed states.

8. The automated cascade impactor as set forth in claim 7, wherein:
each one of said plurality of linkage mechanisms is respectively connected to one of said plurality of impactor stages and to an adjacent one of said plurality of impactor stages.

9. The automated cascade impactor as set forth in claim 7, wherein:
said at least one vertically oriented extension guide comprises three vertically oriented extension guides disposed within a substantially triangular circumferentially symmetrical array around said plurality of impactor stages.

10. The automated cascade impactor as set forth in claim 1, wherein:
each one of said isolation stages is movably mounted upon an isolation armature; and
said isolation armature is operatively connected to said isolation actuator such that when said isolation actuator is actuated in a first direction, said plurality of isolation stages are inserted into said spaces respectively defined between said plurality of impactor stages, and when said isolation actuator is actuated in a second opposite direction, said plurality of isolation stages are removed from said spaces respectively defined between all of said plurality of impactor stages.

11. The automated cascade impactor as set forth in claim 10, further comprising:
a plurality of stop members fixedly mounted at vertically spaced positions upon said isolation armature so as to define stop locations for said plurality of isolation stages as said plurality of isolation stages move downwardly along said isolation armature when said plurality of impactor stages are permitted to move to said separated states whereby said plurality of isolation stages will be properly vertically aligned with said plurality of spaces respectively defined between said plurality of impactor stages, when said plurality of impactor stages are disposed in said separated states, such that said plurality of isolation stages can again be re-inserted into said spaces respectively defined between said plurality of impactor stages.

12. The automated cascade impactor as set forth in claim 1, wherein:
each one of said plurality of impactor stages has a substantially circular configuration of a predetermined diametrical extent; and
each one of said plurality of isolation stages has a substantially annular configuration, with a diametrical extent that is substantially the same as said diametrical extent of each one of said plurality of impactor stages, with upper and lower sealing surfaces of each one of said plurality of isolation stages adapted to sealingly engage upper and lower surface portions of each one of said plurality of impactor stages so as to define an isolated internal volume portion upon each one of said impactor stages when said plurality of impactor stages and said plurality of isolation stages are disposed in said compressed states.

13. The automated cascade impactor as set forth in claim 12, further comprising:
a fluid duct operatively associated with each one of said plurality of isolation stages and fluidically connected to said isolated internal volume portion of a respective one of said plurality of impactor stages when said plurality of impactor stages and said plurality of isolation stages are disposed in said compressed states.

14. The automated cascade impactor as set forth in claim 13, wherein:
said fluid duct, operatively associated with a respective one of said plurality of isolation stages and fluidically connected to said isolated internal volume portion of said respective one of said plurality of impactor stages when said plurality of impactor stages and said plurality of isolation stages are disposed in said compressed states, can supply and extract a fluid drug collection agent to said isolated internal volume portion of said respective one of said plurality of impactor stages, can supply a fluid cleaning agent to said isolated internal volume portion of said respective one of said plurality of impactor stages, and can supply a fluid drying agent to said isolated internal volume portion of said respective one of said plurality of impactor stages.

15. The automated cascade impactor as set forth in claim 14, further comprising:
an oscillation mechanism operatively connected to said cascade impactor so as to facilitate said drug collection, said cleaning, and said drying operations.

16. The automated cascade impactor as set forth in claim 15, wherein:
said oscillation mechanism comprises a motion-inducing mechanism which causes said cascade impactor to undergo movement in several different modes.

17. The automated cascade impactor as set forth in claim 16, wherein:
said several different modes of movement comprise one of rotation, shaking, and vibrating.

18. The automated cascade impactor as set forth in claim 17, wherein:
said rotation can occur around one of a horizontal axis, a vertical axis, and a conical axis.

19. The automated cascade impactor as set forth in claim 15, wherein:
said oscillation mechanism comprises a pneumatic cylinder.

20. The automated cascade impactor as set forth in claim 15, wherein:
said oscillation mechanism comprises a pneumatic cylinder operatively connected to said cascade impactor by pivotally mounted linkage pins and a ball joint.

21. The automated cascade impactor as set forth in claim 15, wherein:

said oscillation mechanism comprises a plurality of sequentially mounted push pins.

* * * * *